United States Patent [19]

DeGrate

[11] Patent Number: 5,932,230

[45] Date of Patent: Aug. 3, 1999

[54] TOPICAL ANALGESIC FORMULATION CONTAINING FRUITS, OILS AND ASPIRIN

[76] Inventor: Frenchell DeGrate, 13280 W. Dr., Desert Hot Springs, Calif. 92240

[21] Appl. No.: 08/878,873

[22] Filed: Oct. 28, 1997

Related U.S. Application Data

[60] Provisional application No. 60/047,227, May 20, 1997.
[51] Int. Cl.$^6$ ...................................................... A61K 7/00
[52] U.S. Cl. ....................... 424/401; 424/404; 424/195.1; 514/886; 514/887; 514/783; 514/969; 514/787; 514/788.1
[58] Field of Search ................................... 424/402, 195.1, 424/404; 524/887, 787, 783, 969, 788.1, 886

[56] References Cited

U.S. PATENT DOCUMENTS

| | | |
|---|---|---|
| 4,505,902 | 3/1985 | Millard . |
| 4,952,560 | 8/1990 | Kigasawa et al. . |
| 5,487,899 | 1/1996 | Davis . |
| 5,503,825 | 4/1996 | Lane . |
| 5,614,561 | 3/1997 | Martin . |

*Primary Examiner*—Thurman K. Page
*Assistant Examiner*—Brian K. Seidleck

[57] ABSTRACT

An analgesic cosmetic formulation in the form of an ointment, salve or cream which is applied to the skin, including the hands and feet for the treatment of such conditions as redness, swelling, itching and soreness of the skin. The cosmetic formulation contains ingredients including oranges, avocado, watermelon, banana, lemon, palm oil, coconut oil, petroleum jelly, beeswax, aloe vera, vitamin E, aspirin, ammonium sulfate, sodium bisulfate and quine sulfate.

1 Claim, No Drawings

TOPICAL ANALGESIC FORMULATION CONTAINING FRUITS, OILS AND ASPIRIN

This application claims the benefit of U.S. Provisional Application No. 60/047,227, filed May 20, 1997.

The present invention is directed to the use of a cosmetic formulation in the form of an ointment, cream or salve. The cosmetic formulation is used for the treatment of various conditions including: cuts; burns; the removal of dry dead skin cells; redness, swelling and soreness of the skin; odor control, itching; fungus; athlete's foot; ingrown toenails; corns; callouses; and hemorrhoids.

The essential ingredients used to treat the abovementioned conditions comprise: fruits, including orange, avocado, watermelon, banana and lemon; vegetables; palm and coconut oils; petroleum jelly; beeswax; aloe vera; vitamin E; aspirin; ammonium sulfate; sodium bisulfate; quine sulfate.

The method by which the cosmetic formulation is made, comprising the steps of:

1. Adding the following ingredients to a five gallon container of water: five pounds of aloe vera; five pounds of oranges; five pounds of avocado; five pounds of palm oil; five pounds of watermelon; five pounds of banana; and five pounds of coconut oil;
2. Adding aspirin; ammonium sulfate and quine sulfate;
3. Cook the above mixture until soft;
4. Blind slowly;
5. Cook again;
6. Strain pulp;
7. Dry pulp;
8. Liquid pulp;
9. Mix in petroleum jelly;
10. Bring to a boil;
11. Let cool and fill in suitable container.

The cosmetic formulation is applied gently on the skin, including the hands and feet as an ointment, salve or cream.

I claim:

1. A topical cosmetic formulation consisting essentially of orange, avocado, watermelon, banana, lemon; palm oil, coconut oil, petroleum jelly; beeswax; aloe vera; vitamin E; aspirin; ammonium sulfate; sodium bisulfate; and quine sulfate.

* * * * *